US00PP18523P2

(12) United States Plant Patent
Farrow

(10) Patent No.: US PP18,523 P2
(45) Date of Patent: Feb. 26, 2008

(54) ***CORNUS* PLANT NAMED 'FARROW'**

(50) Latin Name: *Cornus baileyii*
Varietal Denomination: Farrow

(75) Inventor: Michael W. Farrow, Earleville, MD (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 11/494,160

(22) Filed: Jul. 27, 2006

(51) Int. Cl.
*A01H 5/00* (2006.01)

(52) U.S. Cl. ..... Plt./220

(58) Field of Classification Search ..... Plt./220
See application file for complete search history.

*Primary Examiner*—Kent Bell
(74) *Attorney, Agent, or Firm*—C. A. Whealy

(57) ABSTRACT

A new and distinct cultivar of *Cornus* plant named 'Farrow', characterized by its compact upright plant habit; freely basal branching habit; dense and bushy appearance; and red-colored stems.

1 Drawing Sheet

Botanical designation: *Cornus baileyii.*
Cultivar denomination: 'Farrow'.

BACKGROUND OF THE INVENTION

The present invention relates to a new and distinct cultivar of *Cornus,* grown as an ornamental shrub, botanically known as *Cornus baileyii* and hereinafter referred to by the name 'Farrow'.

The new *Cornus* is a product of a planned breeding program conducted by the Inventor in Earleville, Md. The objective of the breeding program was to develop new *Cornus* cultivars with improved growth habit.

The new *Cornus* originated from an open-pollination during the summer of 2001 of an unnamed seedling selection of *Cornus baileyii,* not patented, as the female, or seed, parent with an unknown selection of *Cornus baileyii.* The new *Cornus* was discovered and selected by the Inventor from within the progeny of the stated open-pollination in a controlled environment in Earleville, Md. during the summer of 2002.

Asexual reproduction of the new *Cornus* by softwood cuttings in a controlled environment in Earleville, Md., has shown that the unique features of this new *Cornus* are stable and reproduced true to type in successive generations.

SUMMARY OF THE INVENTION

The cultivar Farrow has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Farrow'. These characteristics in combination distinguish 'Farrow' as a new and distinct cultivar of *Cornus:*

1. Compact upright plant habit.
2. Freely basal branching habit; dense and bushy appearance.
3. Red-colored stems.

Plants of the new *Cornus* differ from plants of the female parent selection in the following characteristics:

1. Plants of the new *Cornus* are more compact than and not as leggy as plants of the female parent selection.
2. Plants of the new *Cornus* are more freely branching and denser than plants of the female parent selection.

Plants of the new *Cornus* can also be compared to plants of the cultivar Bailey's Dogwood, not patented. Plants of the new *Cornus* differ from plants of the cultivar Bailey's Dogwood in the following characteristics:

1. Plants of the new *Cornus* are more compact and denser than and not as leggy and open as plants of the cultivar Bailey's Dogwood.
2. Plants of the new *Cornus* are more freely basal branching than plants of the cultivar Bailey's Dogwood.
3. Plants of the new *Cornus* have shorter internodes than plants of the cultivar Bailey's Dogwood.
4. Plants of the new *Cornus* have smaller leaves than plants of the cultivar Bailey's Dogwood.

BRIEF DESCRIPTION OF THE PHOTOGRAPHS

The accompanying colored photographs illustrate the overall appearance of the new *Cornus,* showing the colors as true as it is reasonably possible to obtain in colored reproductions of this type. Colors in the photographs may differ slightly from the color values cited in the detailed botanical description which accurately describe the colors of the new *Cornus.*

The photograph at the top of the sheet comprises a side perspective view of a typical plant of 'Farrow' grown during the summer in an outdoor nursery.

The photograph at the bottom of the sheet is a side perspective view of a typical plant of 'Farrow' grown during the winter in an outdoor nursery.

DETAILED BOTANICAL DESCRIPTION

The aforementioned photographs and following observations, measurements and values describe plants grown in Grand Haven, Mich., under commercial practice in an outdoor nursery. Plants had been growing for about 3.5 years when the photographs and description were taken. In the following description, color references are made to The Royal Horticultural Society Colour Chart, 1995 Edition, except where general terms of ordinary dictionary significance are used.

Botanical classification: *Cornus baileyii* cultivar Farrow.

Parentage:

*Female, or seed, parent.*—Unnamed seedling selection of *Cornus baileyii,* not patented.

*Male, or pollen parent.*—Unknown selection of *Cornus baileyii,* not patented.

Propagation:

*Type.*—By softwood cuttings.

*Time to initiate roots.*—About 20 days at 24° C.

*Time to produce a rooted young plant.*—About three months at 24° C.

*Root description.*—Fine to thick; white in color.

*Rooting habit.*—Freely branching; dense.

Plant description:

*Plant form/habit.*—Compact and upright subshrub. Freely basal branching habit, about 65 lateral branches per plant; dense and bushy appearance. Moderately vigorous growth habit.

*Plant height.*—About 75 cm.

*Plant width* (*spread*).—About 1 meter.

*Lateral branches.*—Length: About 50 cm. Diameter: About 3 mm. Internode length: About 3.5 cm. Strength: Strong. Texture: Smooth, glabrous. Color: 183A.

Foliage description:

*Arrangement.*—Opposite, simple.

*Length.*—About 10 cm.

*Width.*—About 6.2 cm.

*Shape.*—Ovate.

*Apex.*—Acute.

*Base.*—Obtuse.

*Margin.*—Entire.

*Texture, upper and lower surfaces.*—Smooth, glabrous.

*Venation pattern.*—Pinnate.

*Color.*—Developing and fully developed leaves, upper surface: 137A; venation, 137A. Developing and fully developed leaves, lower surface: 147B; venation, 145B.

*Petiole.*—Length: About 2.8 cm. Diameter: About 2 mm. Texture, upper and lower surfaces: Smooth, glabrous. Color, upper and lower surfaces: 183C.

Flower description: Flower initiation and development has not been observed on plants of the new *Cornus.*

Disease/pest resistance: Plants of the new *Cornus* have not been noted to be resistant to pathogens and pests common to *Cornus.*

Temperature tolerance: Plants of the new *Cornus* have been observed to tolerate temperatures from about −26° C. to about 35° C.

It is claimed:

1. A new and distinct *Cornus* plant named 'Farrow' as illustrated and described.

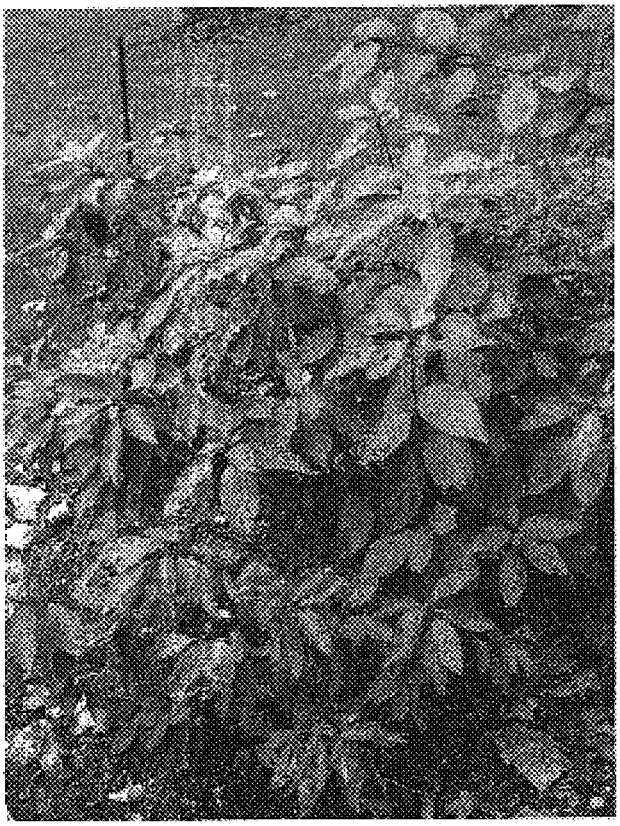
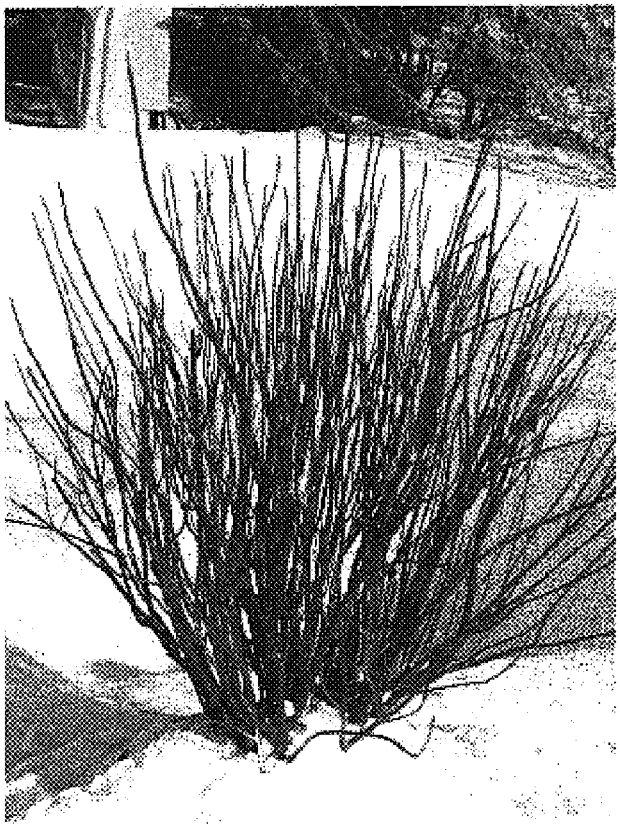

* * * * *